US009616417B2

(12) United States Patent
Teketel et al.

(10) Patent No.: US 9,616,417 B2
(45) Date of Patent: Apr. 11, 2017

(54) CATALYST FOR THE CONVERSION OF OXYGENATES TO OLEFINS AND A PROCESS FOR PREPARING SAID CATALYST

(75) Inventors: Shewangizaw Teketel, Oslo (NO); Stian Svelle, Oslo (NO); Pablo Beato, Oslo (NO)

(73) Assignee: Haldor Topsoe A/S, Lyngby (DK)

( * ) Notice: Subject to any disclaimer, the term of this patent is extended or adjusted under 35 U.S.C. 154(b) by 156 days.

(21) Appl. No.: 14/234,370

(22) PCT Filed: Jul. 20, 2012

(86) PCT No.: PCT/EP2012/064300
§ 371 (c)(1),
(2), (4) Date: Jan. 22, 2014

(87) PCT Pub. No.: WO2013/014081
PCT Pub. Date: Jan. 31, 2013

(65) Prior Publication Data
US 2014/0179971 A1    Jun. 26, 2014

(30) Foreign Application Priority Data
Jul. 22, 2011    (DK) .................................. 2011 00565

(51) Int. Cl.
*B01J 21/12*    (2006.01)
*C01B 39/00*    (2006.01)
(Continued)

(52) U.S. Cl.
CPC ............... *B01J 29/70* (2013.01); *B01J 37/06* (2013.01); *C07C 1/20* (2013.01); *C07C 1/22* (2013.01);
(Continued)

(58) Field of Classification Search
CPC .. B01J 21/12; B01J 29/70; C07C 1/20; C01B 39/00
(Continued)

(56) References Cited

U.S. PATENT DOCUMENTS 5,118,483 A    6/1992    Barri

FOREIGN PATENT DOCUMENTS

EP    0 353 915 A2    2/1990
EP    0 706 984 A1    4/1996
(Continued)

OTHER PUBLICATIONS

"Organotemplate-free Hydrothermal Synthesis of SUZ-4 Zeolite: Influence of Synthesis Conditions," Hualan Zhou et al. Chinese Journal of Chemical Engineering, 22(1), pp. 120-126 (2014).*
(Continued)

*Primary Examiner* — Patricia L Hailey
(74) *Attorney, Agent, or Firm* — Blank Rome LLP

(57) ABSTRACT

A catalyst for the conversion of oxygenates, such as alcohols or ethers, to olefins consists essentially of a selected SUZ-4 zeolite that has a Si/Al ratio of at least 20, preferably between 20 and 500, especially between 20 and 100. The basic SUZ-4 zeolite is prepared in a manner known per se, whereafter the Si/Al ratio is increased to the desired value. The selected SUZ-4 zeolite catalyst of the invention has a longer life time and a better product selectivity than the conventional/standard SUZ-4 zeolite catalysts.

8 Claims, 3 Drawing Sheets

(51) Int. Cl.
  *B01J 29/70* (2006.01)
  *B01J 37/06* (2006.01)
  *C07C 1/20* (2006.01)
  *C07C 1/22* (2006.01)

(52) U.S. Cl.
  CPC ........ *B01J 2229/16* (2013.01); *B01J 2229/36* (2013.01); *B01J 2229/37* (2013.01); *C07C 2529/70* (2013.01)

(58) Field of Classification Search
  USPC .................. 502/64, 263; 423/700, 713, 714; 585/638–640
  See application file for complete search history.

(56) References Cited

FOREIGN PATENT DOCUMENTS

| JP | 2011-62664 A | 3/2011 |
|----|--------------|--------|
| WO | WO 03/064354 A1 | 8/2003 |
| WO | WO 2007/105875 A1 | 9/2007 |

OTHER PUBLICATIONS

"Synthesis and Proposed Framework Topology of Zeolite SUZ-4," Stephen L. Lawton et al. J. Chem. Soc., Chem. Commun., 1993, pp. 894-896.*

"Fast crystallization of SUZ-4 Zeolite with Hydrothermal Synthesis: Part I Temperature and Time Effect," P. Vongvoradit et al. Procedia Engineering 32 (2012), pp. 198-204.*

"The first study on the synthesis of uniform SUZ-4 zeolite nanofiber," Shan Gao et al. Microporous and Mesoporous Materials 159 (2012), pp. 105-110.*

"Green synthesis of SUZ-4 zeolite controllable in morphology and $SiO_2/Al_2O_3$ ratio," Shan Gao et al. Microporous and Mesoporous Materials 174 (2013), pp. 108-116.*

A. Subbiah et al., "$NO_x$ Reduction Over Metal-Ion Exchanged Novel Zeolite Under Lean Conditions: Activity and Hydrothermal Stability." Applied Catalysis B: Environmental, vol. 42, pp. 155-178, 2003.

S. Jiang et al., "Zeolite SUZ-4 as Selective Dehydration Catalyst for Methanol Conversion to Dimethyl Ether." Chemistry Letters, vol. 33, No. 8, pp. 1048-1049, 2004.

S. Jiang et al., "Effect of Dealumination on Acidic and Catalytic Properties of HK-SUZ-4." Journal of Dalian Maritime University, vol. 33, No. 4, pp. 118-121, Nov. 2007.

M.A. Asensi et al., "Zeolite SUZ-4: Reproducible Synthesis, Physicochemical Characterization and Catalytic Evaluation for the Skeletal Isomerization of $n$-butenes." Microporous and Mesoporous Materials, vol. 28, pp. 427-436, 1999.

Chen, M., et al., "Dehydrogenation of Propane Over Spinel-Type Gallia-Alumina Solid Solution Catalysts", Journal of Catalysis 256 (2008) pp. 293-300.

Corbin, D.R., et al., "Comparison of Analytical Techniques for The Determination of Silicon and Aluminum Content In Zeolites", American Chemical Society 59 (1987) pp. 2722-2728.

\* cited by examiner

CATALYST FOR THE CONVERSION OF OXYGENATES TO OLEFINS AND A PROCESS FOR PREPARING SAID CATALYST

TECHNICAL FIELD

The present invention relates to a catalyst, which is suitable for use in the process where oxygenates, i.e. chemical compounds containing oxygen as part of their structure (e.g. alcohols or ethers) are converted to olefins. A method for the formation of the catalyst is also provided.

More specifically the invention concerns a catalyst for the conversion of oxygenates to olefins, said catalyst being based on SUZ-4 zeolite. The SUZ-4 zeolite is modified in a number of ways with the purpose to yield a catalyst with improved properties for the conversion of oxygenates to olefins.

BACKGROUND TO THE INVENTION

SUZ-4 zeolite has been given the three-letter IUPAC designation code SZR. The framework of the SUZ-4 zeolite consists of 4-, 5-, 6-, 8- and 10-membered rings of 3-dimensional channel systems. It has an ortho-rhombic unit cell with dimensions of a=18.8696, b=14.4008 and c=7.5140 Å, respectively. The 10-membered ring channels of the SUZ-4 zeolite are the main straight channels in the framework, and they are interconnected by zig-zag 8-ring channels. The 10-ring straight channels of the SUZ-4 zeolite have dimensions of 4.6×5.2 Å, i.e. notably smaller than the 10-ring channels found in the ZSM-5 zeolite (5.3×5.5 and 5.4>5.6 Å).

Within the catalyst area, the SUZ-4 zeolite is known to be a selective and stable dehydration catalyst in the process for producing dimethyl ether from methanol (Jiang, S. et al., Chemistry Letters 33, no. 8, 1048 (2004)).

According to U.S. Pat. No. 6,936,562 B2 (General Motors Corp.), certain metal-exchanged SUZ-4 zeolites have been prepared which have catalytic activity in the reduction of $NO_x$ in the exhaust gas from a hydrocarbon or alcohol fuelled engine.

Similar hydrothermally-stable catalysts based on substituted SUZ-4 zeolites are described in the related U.S. Pat. No. 6,645,448 B2 (General Motors Corp.), and in U.S. Pat. No. 5,118,483 B2 (British Petroleum Co.) various crystalline forms of the SUZ-4 zeolite based on crystalline (metallo) silicates are described. It should be noted that—with reference to e.g. U.S. Pat. No. 5,118,483—the standard methods for forming SUZ-4 zeolites will usually provide thermochemically-preferred Si/Al stoichiometries, regardless of the molar ratios of the Si and Al components in the starting materials.

EP 0 706 984 A1 (BP Chemicals Ltd.) discloses the catalytic use of SUZ-4 zeolite for the isomerisation of hydrocarbons, and in U.S. Pat. No. 6,514,470 B2 (University of California) a large number of aluminium-silicate materials, including SUZ-4 zeolite, are used as catalysts for lean burn exhaust abatement. JP 2009-233620 A (Tosoh Corp.) describes the use of SUZ-4 zeolite in an SCR catalyst with the objective to give the catalyst improved hydrothermal durability.

Most recently, variants of the methanol to olefins (MTO) process have been disclosed in EP 1 963 241 A2 and in WO 2008/042616 A2 (both to UOP LLC).

One of the main challenges within the field of MTO catalysis is that the known catalysts have a very limited life span, requiring continuous regeneration at elevated temperature which eventually lead to irreversible damage to the catalyst. According to the inventors, this is also the case with the SUZ-4 zeolite-based catalysts, because the life span of the current SUZ-4 zeolite-based catalyst prepared using the standard methods in the MTO catalysis field does not exceed that of other catalysts such as silicoaluminophosphate molecular sieves (e.g. SAPO-34). However, it has now surprisingly been found that the life span of the SUZ-4 zeolite-based catalyst for MTO use can be markedly improved by either modification of the zeolite acidity (i.e. by increasing the Si/Al ratio, partial ion-exchange of alkali counter-ions)

SUMMARY OF THE INVENTION

The invention concerns a catalyst for the conversion of oxygenates to olefins, said catalyst consisting essentially of a selected SUZ-4 zeolite. The catalyst according to the invention is characterised in that the zeolite has a Si/Al ratio of at least 20, preferably between 20 and 500. The most preferred Si/Al ratio in the zeolite is between 20 and 100.

Furthermore, the invention concerns a process for the preparation of the catalyst, said method comprising the steps of:

(a) providing a conventional/standard SUZ-4 zeolite having a Si/Al ratio of less than 20, and
(b) increasing the Si/Al ratio to 20 or above by contacting the product of step (a) with water vapour at elevated temperatures.

In the above process, step (b) is preferably performed at a temperature of 400-700° C. Furthermore it is preferred to perform step (b) for 1-12 hours by feeding 1-20 g $H_2O$ per g of catalyst per hour.

The SUZ-4 catalyst resulting from step (b) of the process is preferably washed with an aqueous acid solution.

The catalyst according to the invention is used for the conversion of oxygenates to olefins. The oxygenates to be converted to olefins are preferably selected from the group consisting of C1 to C4 alcohols. The most preferred oxygenate to be converted to an olefin is methanol.

DETAILED DESCRIPTION OF THE INVENTION

Figure 1:
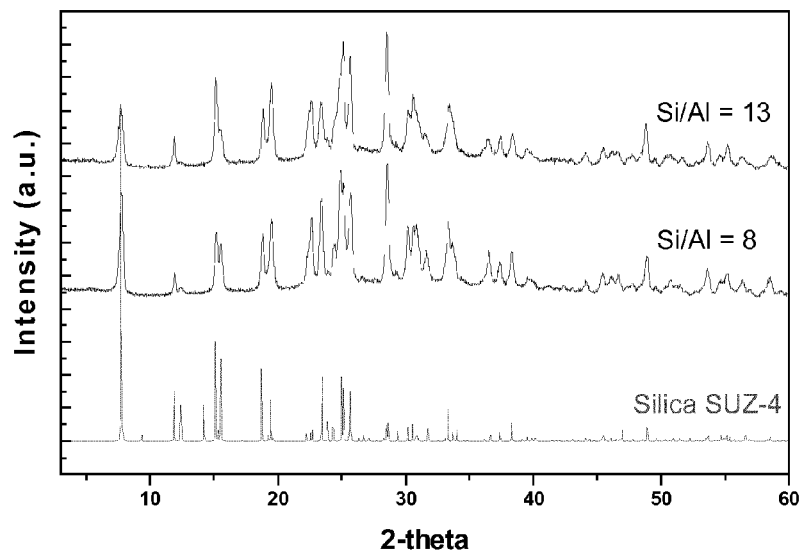
FIG. 1 shows the XRD diffraction profile of SUZ-4 having gel Si/Al=8 and 13.

According to the invention the selected SUZ-4 zeolite has a Si/Al ratio of at least 20, preferably between 20 and 500 as determined using SEM-EDX, ICP and ammonia TPD. A more preferred Si/Al ratio is between 20 and 100.

The SUZ-4 zeolite-based catalyst is synthesized in a manner known per se by preparing (i) a solution of Al-wire in aqueous MOH, where M is an alkali metal, (ii) a 25 wt % solution of tetraethylammonium hydroxide (TEAOH) and (iii) a 40 wt % solution of Ludox-AS 40, mixing the solutions (i)-(iii) at 60° C. and crystallizing the resultant gel at 160° C. with stirring, followed by (iv) ion-exchange to remove the M ions completely from the material and (v) calcination to obtain the zeolite in hydrogen form. According to the invention, this standard method gives a H-SUZ-4 catalyst with high density of acid sites, and it deactivates very rapidly during oxygenate (methanol) conversion to olefins. It should be noted that the conversion of methanol to olefins is novel in this work, the drawback is the rapid deactivation. Thus, the Si/Al ratio is then adjusted to the desired value by changing the amount of Al-wire dissolved in the aqueous MOH solution (i). The Si/Al ratio can also be adjusted to the desired value another way, i.e. by contacting the product with water vapour at elevated temperatures (so-called "steaming"). The steaming is preferably performed for a period of 1-12 hours by feeding 1-20 g $H_2O$ per g of catalyst per hour at a temperature of 400-700° C. After the steaming the resulting SUZ-4 catalyst is washed with an aqueous acid solution.

While it is known from the above citations that SUZ-4 zeolites may be used as catalysts in various contexts, the specific use of SUZ-4 zeolite materials as catalysts in the conversion of oxygenates to olefins is novel. Thus, the present invention is related to the use of the above-mentioned SUZ-4 zeolite material in the conversion of oxygenates, especially methanol/dimethyl ether (DME), to olefins. Due to the unique topology (SZR topology), consisting of a 3-dimensional channel system of straight 10-rings and zig-zag 8-rings, a surprisingly high selectivity (60-70%) to light olefins (ethylene and propylene) is observed. As a by-product (approximately 10-20%), olefins with a hydrocarbon chain length in the gasoline range are obtained. The selectivity to aromatic hydrocarbons is typically below 2%.

As a consequence of the selectivities observed, the catalyst has a high potential to be used as a catalyst for the production of light olefins (ethylene and propylene) with a gasoline fraction having a low content of aromatic compounds as a co-product. Methane, which is also regarded as co-product during olefin production, could be used as a source for the necessary external thermal energy for the MTO process.

The present invention will now be illustrated further in the following examples.

EXAMPLE 1

(A) Synthesis of SUZ-4 Zeolite Using the Standard Method

An SUZ-4 zeolite was synthesized according to the procedure published by S. Jiang et al., Chemistry Letters 33, no. 8, 1048 (2004).

The following solutions were prepared:
(a) 0.4 g Al-wire dissolved in a KOH solution (3.3 g KOH in 50.6 g $H_2O$)
(b) 7.93 g TEAOH (25 wt %)
(c) 18.23 g LUDOX AS-40 (40 wt %).

To the clear solution (a), solution (b) and solution (c) were added successively while stirring at 60° C. The batch composition of the synthesis mixture was 7.92 $K_2O$:$Al_2O_3$:16.21 $SiO_2$:1.83 TEAOH:507 $H_2O$.

The gel was transferred to 40 ml Teflon lined stainless steel autoclaves. The Si/Al ratio was varied by changing the amount of Al-wire dissolved in KOH solution. Crystallization of the gel was carried out under horizontal stirring conditions using a Teflon coated bar magnet at 160° C. for 2 to 5 days. When the crystallization was complete, the reaction mixture was washed with distilled water, and the product was recovered by filtration. The calcined material as prepared was subjected to ion-exchange three times with an aqueous 1N $NH_4NO_3$ solution under reflux, washed with deionized water, dried at 120° C. for 3 hours and then calcined at 550° C. for 12 hours. The synthesis conditions used are summarized in table 1 below.

TABLE 1

Synthesis conditions used in the crystallization of SUZ-4 zeolite

| Synth. No. | Si/Al gel | Cryst. time | Cryst. conditions* | Result* |
|---|---|---|---|---|
| SUZ4-1 | 8 | 2 days | H.S. | SUZ-4a |
| SUZ4-2 | 8 | 5 days | H.S. | SUZ-4 |
| SUZ4-3 | 13 | 3 days | H.S. | SUZ-4 |
| SUZ4-4 | 17 | 2 days | H.S. | Amorph. |

*In the above table, H.S. means horizontal stirring, and SUZ-4a means SUZ-4 + amorphous.

(B) Characterization and Catalyst Tests

X-Ray Diffraction

The purity and crystallinity of the products were identified using X-ray diffraction on a Siemens D-5000 diffractometer with Bragg-Brentano geometry, position sensitive detector and CuKα1 radiation ($\lambda$=1.5406 Å). X-ray diffraction (XRD) data were analyzed using EVA 8.0, developed by SOCABIM. The diffraction pattern was compared with the data in the powder diffraction file (PDF) database compiled and revised by Joint Committee on Powder Diffraction Standards International Centre.

Surface Area

The BET surface area of the SUZ-4 catalysts was determined by nitrogen adsorption at a temperature of 77 K using a BELSORP-mini II instrument. Prior to the measurement the catalyst was pretreated for 5 hours (out-gassing for 1 hour at 80° C. and for 4 hours at 300° C.).

Scanning and Transmission Electron Microscopy

SUZ-4 crystals were sprinkled on a carbon tape mounted on a copper grid. The crystal size and shape were investigated using Scanning Electron Microscopy, Quanta 200 F (FEI). Similarly TEM images were taken and electron diffraction revealed unit cell parameters and orientation of the 8- and 10-ring channels within the crystal.

The template was removed by calcination under static air at 550° C. for 6 hours. The calcined samples were ion-exchanged for 3×2 hours with 1M $NH_4NO_3$ in a 70° C. water bath. The ion-exchanged catalysts were calcined at 550° C. for 2 hours in static air, for 1 hour ex situ in a flow of pure oxygen, and for 1 hour in situ in the fixed bed reactor in a flow of pure oxygen prior to each catalytic experiment to desorb ammonia.

The calcined SUZ-4 catalysts were tested for the MTH reaction using a fixed bed reactor. 50 mg of catalysts and temperatures between 350 and 450° C. were used. The catalysts were pressed, gently crushed and sieved to a particle size of 0.25-0.42 mm. Before each test, the catalysts were calcined in situ at 550° C. (see above) under a flow of oxygen for 1 hour. Helium was used as a carrier gas and methanol was fed using a bubble saturator placed in a water bath at 20° C. A methanol feed rate (expressed as WHSV, i.e.

weight hourly space velocity, which is defined as the weight of feed flowing per unit weight of the catalyst per hour) of 2.05 $gg^{-1}h^{-1}$ was used.

The reaction products were analyzed by GC and GC-MS. The GC analyses were performed using an on-line gas chromatograph (Agilent 6890 A with FID) using a Supelco SPB-5 capillary column (60 m, 0.530 mm i.d., stationary phase thickness 3 μm). The temperature was programmed between 45 and 260° C. with a heating rate of 25° C. $min^{-1}$ (hold time 5 min at 45° C. and 16 min at the final temperature). GC-MS analyses were performed using a HP 6890 gas chromatograph equipped with a GS-GASPRO column (60 m, 0.32 mm) and a HP-5973 Mass Selective Detector. Each analysis took 40 minutes, and the temperature was programmed between 100 and 250° C. with a heating rate of 10° C. $min^{-1}$ (hold time 10 min at 100° C. and 15 min at 250° C.)

(C) Results

FIG. 1 displays the XRD profiles of SUZ-4 having Si/Al ratios of 8 and 13 in the synthesis gel. By comparing the observed diffraction profile with a theoretically calculated diffraction profile (FIG. 1 bottom), it was observed that the product was free from structural impurities.

Figure 2:
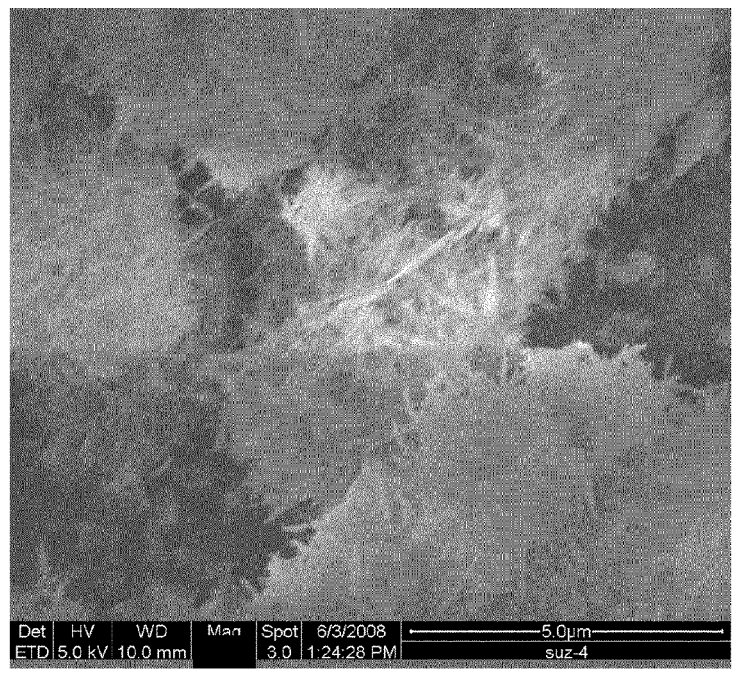
FIG. 2 shows an SEM image of SUZ-4 having Si/Al=8 in the synthesis gel.
Figure 3:
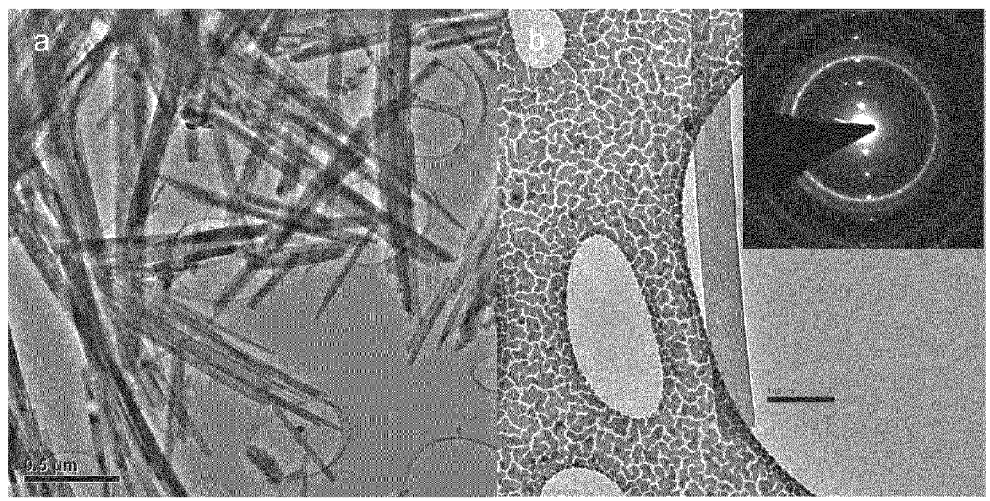
FIG. 3 shows a TEM image of an SUZ-4 zeolite-based catalyst having Si/Al=8 in the synthesis gel.

FIG. 2 and FIG. 3 respectively displays the SEM and TEM image of an SUZ-4 zeolite-based catalyst having Si/Al=8 in the synthesis gel. The crystals were needle-shaped and ~2-3 μm in length.

FIG. 3 displays (a) TEM overview micrograph. (b) Micrograph and diffraction image (insert) of random crystallite.

Figure 4:
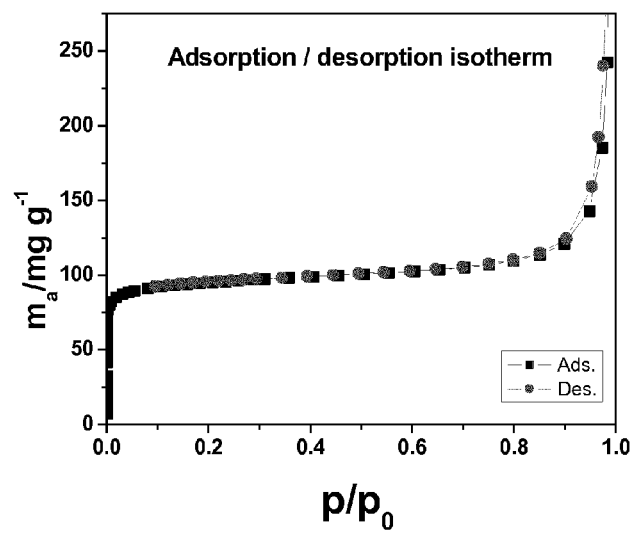
FIG. 4 shows the BET isotherm of SUZ-4 having gel Si/Al=8 in the synthesis gel.

FIG. 4 displays the BET isotherm for the SUZ-4 catalyst having Si/Al=8. The isotherm is typical for a microporous material. The surface area of the catalyst was found to be 346 $m^2/g$.

Figure 5:
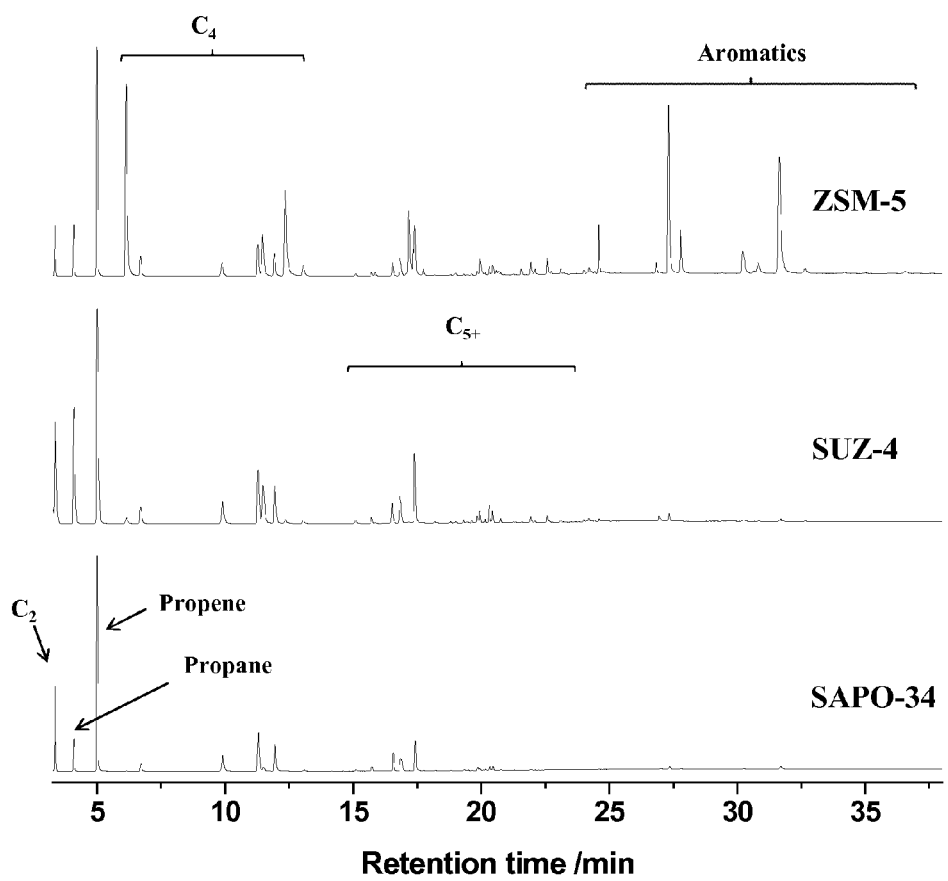
FIG. 5 shows GC-MS chromatograms of SAPO-34, SUZ-4, and ZSM-5 catalysts tested under identical reaction conditions after 5 minutes on stream. NB: C1 is not included in the chromatogram. (400° C. and WHSV=2.05 $gg^{-1}h^{-1}$)

FIG. 5 displays GC-MS chromatograms of the methanol to hydrocarbon reaction over different zeolites, reaction carried out under identical conditions.

EXAMPLE 2

Determination of Methanol Conversion

Table 2 below shows the percentage methanol conversion and the product selectivities at different reaction temperatures; WHSV=2.05 $gg^{-1}h^{-1}$ was used. At 350° C. the initial conversion of the catalyst was 83%, and the catalyst showed a very high selectivity for C1 (21%, second most abundant species). Increasing the temperature to 400 and 450° C. improved the initial conversion by the catalyst to ~100%, the selectivity for C1 was decreased by approximately a factor of 2. At these reaction temperatures, C2 and C3 were the most abundant species (C2+C3>60%).

TABLE 2

Methanol conversion, product selectivity and C4 hydrogen transfer index of SUZ-4 catalyst for the MTH reaction at different reaction temperatures after 3 minutes on stream, Si/Al = 8. (WHSV = 2.05 $gg^{-1}h^{-1}$)

| Temp. | Conversion | C1 | C2 | C3 | C4alkene |
|---|---|---|---|---|---|
| 350° C. | 83.0% | 21.34 | 13.56 | 37.48 | 13.04 |
| 400° C. | 99.7% | 10.24 | 24.35 | 37.71 | 14.11 |
| 450° C. | 99.7% | 11.92 | 35.79 | 30.74 | 12.48 |

| Temp. | C4alkane | C5 | C6+ | C4HTI |
|---|---|---|---|---|

TABLE 2-continued

Methanol conversion, product selectivity and C4 hydrogen transfer index of SUZ-4 catalyst for the MTH reaction at different reaction temperatures after 3 minutes on stream, Si/Al = 8. (WHSV = 2.05 $gg^{-1}h^{-1}$)

| 350° C. | 1.85 | 7.04 | 5.68 | 0.12 |
|---|---|---|---|---|
| 400° C. | 2.60 | 7.78 | 3.20 | 0.16 |
| 450° C. | 1.36 | 5.19 | 2.53 | 0.10 |

It is firmly believed that the high selectivity towards C2 and C3 is caused by the needle-like morphology of the catalyst crystals, as seen by SEM. A simulation of crystal growth indicates that the 10-ring channels run in the direction of the needles. If these needles are described as cylinders, the simulation result means that only the two bases of each cylinder serve as exits through 10-ring channels. The major part of the external crystal surface will serve as exits through 8-rings, which are orthogonal to the 10-rings. This gives rise to a product shape selectivity dominated by 8-rings, leading to high selectivities towards C2 and C3.

The SUZ-4 sample tested deactivates very fast. After 43 minutes (the effluent is sampled every 40 minutes), the conversion was negligible. This is consistent with the relatively high selectivity towards C1 (and also propane), which is inherently linked to formation of aromatics and coke. This rapid deactivation may well be attributed to the very high Al content in the sample, which means that the density of acid sites is untypically high for methanol conversion catalysts.

EXAMPLE 3

Comparison of SUZ-4 to ZSM-5 and SAPO-34

For the sake of comparison, ZSM-5 and SAPO-34 were tested for the MTH reaction under identical reaction conditions as those of SUZ-4, and the results are presented in FIG. 5 and Table 3. Note that SAPO-34 is currently used as a commercial MTO catalyst. Table 3 displays the product selectivities for the three different zeolites at 400° C. The GC analyses were performed after 3 minutes on stream, and the catalysts displayed approximately 100% conversion. ZSM-5 catalyst has high selectivity for heavier hydrocarbons than SUZ-4 and SAPO-34 catalysts (see FIG. 5 and Table 3).

TABLE 3

Product selectivity of the MTH reaction over ZSM-5, SAPO-34, and SUZ-4 catalysts, WHSV = 2, 400° C., and full conversion of methanol

| Catalyst | C1 | C2 | C3 | C4alkene |
|---|---|---|---|---|
| ZSM-5 | 0.28 | 7.58 | 21.20 | 8.77 |
| SUZ-4 | 10.24 | 24.35 | 37.71 | 14.11 |
| SAPO-34 | 0.56 | 29.65 | 42.59 | 16.70 |

| Catalyst | C4alkane | C5 | C6+ | C4HTI |
|---|---|---|---|---|
| ZSM-5 | 18.15 | 13.19 | 30.83 | 0.67 |
| SUZ-4 | 2.60 | 7.78 | 3.20 | 0.16 |
| SAPO-34 | 1.15 | 7.43 | 1.91 | 0.06 |

The C4 alkane selectivity of the ZSM-5 catalyst is notably higher than both that of the inventive SUZ-4 catalyst and that of the SAPO-34 catalyst, giving rise to a higher C4 hydrogen transfer index. Except for the selectivity for methane (C1), the SAPO-34 and SUZ-4 catalysts showed comparable product selectivities for all the other hydrocarbons. For both materials C2 and C3 were the most abundant species (SAPO-34 C2+C3=72.3 and SUZ-4 C2+C3=61.1). The inventive SUZ-4 catalyst showed a much higher selectivity for methane (approximately 10%) than SAPO-34 (>1%).

The invention claimed is:

1. A zeolite catalyst for converting above 99% of oxygenates to olefins, wherein said catalyst is selective to production of C2 and C3 alkenes and consists essentially of a SUZ-4 needle-shaped zeolite, wherein the zeolite has a bulk molar Si/Al ratio of between above 20 and 500.

2. Catalyst according to claim 1, wherein the zeolite has a bulk molar Si/Al ratio up to 100.

3. A process for the preparation of the needle-shaped catalyst according to claim 1, said method comprising the steps of:
(a) providing a conventional/standard SUZ-4 zeolite gel having a bulk molar Si/Al ratio of less than 20,
(b) adjusting the Si/Al ratio of the conventional/standard SUZ-4 zeolite with a bulk molar ratio of less than 20, either contacting the gel with a different level of aluminum dissolved in a KOH to increase the Si/Al ratio to above 20, and crystallizing (b) to obtain a SUZ-4 zeolite having an Si/Al ratio of greater than 20 and needle shaped crystals, or contacting the gel of step (b) with steam at a temperature of 400-700° C., followed by washing to form needle-shaped crystals.

4. Process according to claim 3, wherein step (b) is performed for 1-12 hours by feeding 1-20 g $H_2O$ per g of catalyst per hour.

5. Process according to claim 3, wherein the SUZ-4 catalyst resulting from step (b) is washed with an aqueous acid solution.

6. A method of converting oxygenates to olefins comprising contacting the catalyst according to claim 1 with a $C_1$ to $C_4$ oxygenate to produce an olefin.

7. The method according to claim 6, wherein the oxygenates are selected from the group consisting of C1 to C4 alcohols.

8. The method according to claim 7, wherein the oxygenate is methanol.

* * * * *

UNITED STATES PATENT AND TRADEMARK OFFICE
CERTIFICATE OF CORRECTION

PATENT NO. : 9,616,417 B2
APPLICATION NO. : 14/234370
DATED : April 11, 2017
INVENTOR(S) : Shewangizaw Teketel et al.

It is certified that error appears in the above-identified patent and that said Letters Patent is hereby corrected as shown below:

On the Title Page

Item [75], should read:
Shewangizaw Teketel, Oslo (NO); Stian Svelle, Oslo (NO); Pablo Beato, Copenhagen (DK)

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*